(12) United States Patent
Fisher

(10) Patent No.: US 6,350,244 B1
(45) Date of Patent: Feb. 26, 2002

(54) BIOABSORABLE MARKERS FOR USE IN BIOPSY PROCEDURES

(75) Inventor: John S. Fisher, Belleair, FL (US)

(73) Assignee: Biopsy Sciences, LLC, Clearwater, FL (US)

( * ) Notice: Subject to any disclaimer, the term of this patent is extended or adjusted under 35 U.S.C. 154(b) by 0 days.

(21) Appl. No.: 09/507,052

(22) Filed: Feb. 21, 2000

(51) Int. Cl.$^7$ ................................................ A61B 10/00
(52) U.S. Cl. ...................................... 600/562; 606/116
(58) Field of Search .............................. 600/407, 420, 600/431, 562, 564; 606/116, 117, 151, 219; 128/897

(56) References Cited

U.S. PATENT DOCUMENTS

| | | | | |
|---|---|---|---|---|
| 5,562,613 A | * | 10/1996 | Kaldany | 604/57 |
| 5,853,366 A | * | 12/1998 | Dowlatshahi | 600/434 |
| 5,902,310 A | * | 5/1999 | Foerster et al. | 606/142 |
| 5,941,890 A | * | 8/1999 | Voegele et al. | 606/151 |
| 6,056,700 A | * | 5/2000 | Burney et al. | 600/564 |
| 6,080,099 A | * | 6/2000 | Slater et al. | 600/8 |
| 6,161,034 A | * | 12/2000 | Burbank et al. | 600/431 |
| 6,173,715 B1 | * | 1/2001 | Sinanan et al. | 128/899 |
| 6,174,330 B1 | * | 1/2001 | Stinson | 623/1.34 |
| 6,181,960 B1 | * | 1/2001 | Jensen et al. | 600/431 |

* cited by examiner

Primary Examiner—John P. Lacyk
Assistant Examiner—Charles Marmor, II
(74) Attorney, Agent, or Firm—Ronald E. Smith; Smith & Hopen, P.A.

(57) ABSTRACT

A bioabsorbable marker is placed in soft tissue such as breast tissue near a lesion during a biopsy procedure. If tests prove the lesion to be malignant, the marker indicates the location of the lesion and the marker is removed surgically together with the lesion. If tests prove the lesion to be benign, there is no need to surgically remove the marker due to its bioabsorbability. One or more markers may be carried in an elongate, flexible marker carrier that is ensheathed within an elongate, flexible outer sheath. The flexible outer sheath is slidingly introduced into the proximal end of a biopsy needle until its distal free end protrudes from a port formed in the distal end of the biopsy needle. Retraction of the outer sheath relative to the marker carrier then exposes the marker carrier. The markers exit the marker carrier under their own inherent bias or an auxiliary bias is employed to eject them from the marker carrier. In a first embodiment, the bioabsorbable markers are hollow spheres made of polylactite acid. They are filled with iodine or other radiopaque material so that they are visible under X-rays and/or ultrasound. The radiopaque material is also bioabsorbable. In an additional embodiment, the hollow spheres are filled with an easily visible dye so that, when punctured, they provide a visible indication of a lesion's location. In another embodiment, they are filled with radioactive material and are inserted for therapeutic purposes in a lesion known to be malignant. Another embodiment provides solid markers, formed by pre-mixing together a radiopaque material and a bioabsorbable material. The solid markers may also include dyes and radioactive materials. In all embodiments, the markers may be spherical, cubical, pyramidal, pentagonal, or any other predetermined shape.

8 Claims, 1 Drawing Sheet

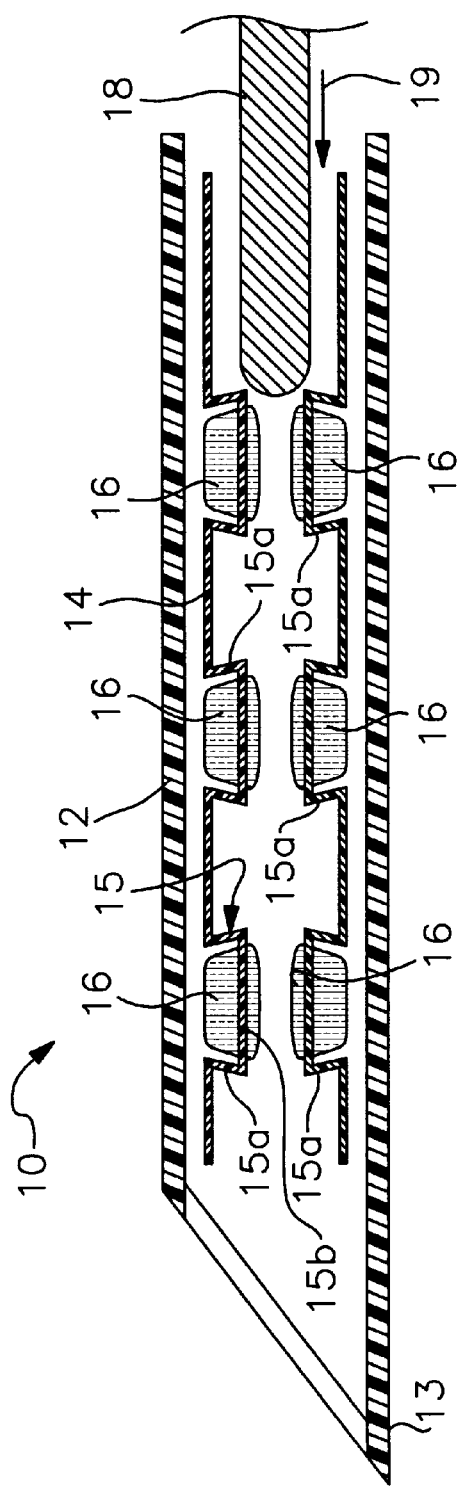
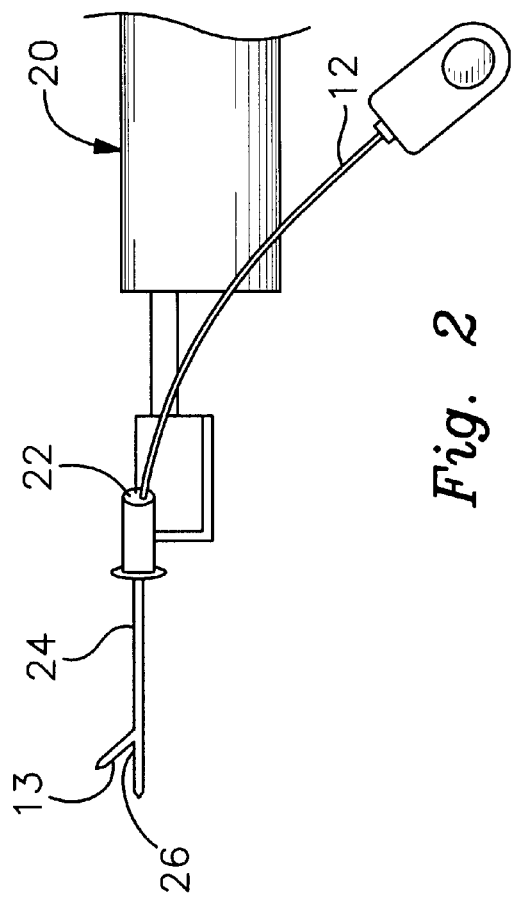
Fig. 1
Fig. 2

BIOABSORABLE MARKERS FOR USE IN BIOPSY PROCEDURES

BACKGROUND OF THE INVENTION

1. Field of the Invention

This invention relates, generally, to the medical arts. More particularly, it relates to an improved marker for marking the location of a lesion in soft tissue in biopsy procedures.

2. Description of the Prior Art

If a mammogram or similar means detects a lesion in soft tissue such as breast tissue, a biopsy must be performed to determine whether or not the lesion is benign or malignant. If benign, no surgical removal thereof is required.

One or more markers to indicate the location of the lesion are left in the breast tissue at the time the biopsy is performed, in the event surgery is needed. Although many different types of markers have been used over the years, a marker now in widespread use is a small metallic member that can be seen under X-rays. If the lab tests indicate that the lesion is malignant, the physician performing the surgical removal of the lesion removes the marker or markers at the same time the lesion is removed.

However, in about eighty percent (80%) of all cases where a biopsy is performed, the lesion is determined to be harmless and no surgical removal thereof is required. The patient is relieved to learn that no surgery is required, but unhappy when advised by the physician that the metallic marker or markers will remain in the breast tissue forever.

Unfortunately, the markers do not always remain in the breast tissue forever. They can migrate to the liver, the heart, the brain, or elsewhere, and cause problems. Surgery may then be needed to remove them. As patients learn about these complications from their physicians or others who have undergone biopsies, they are less inclined to request mammograms.

What is needed, then, is an improved marker for use in biopsies. The marker should be radiopaque so that it is visible under X-rays and/or ultrasound. Moreover, it should be less likely to migrate within the body, and it should never require surgical removal.

However, in view of the prior art, considered as a whole at the time the present invention was made, it was not obvious to those of ordinary skill in the medical arts how such a marker could be provided.

SUMMARY OF THE INVENTION

The long-standing but heretofore unfulfilled need for a biopsy marker that is less likely to migrate within the body and that requires no surgical removal is now fulfilled by a new, useful, and nonobvious invention.

The novel method for delivering markers that indicate the location of a lesion in soft tissue includes the steps of providing an elongate, flexible outer sheath of generally tubular configuration, providing an elongate, flexible marker carrier that is slideably received within the outer sheath, forming at least one marker retaining means in the marker carrier and positioning at least one marker in the at least one marker retaining means. The outer sheath and marker carrier ensleeved therewithin are introduced into an open proximal end of a needle of a biopsy tool. The outer sheath is advanced until a distal free end thereof extends through a port formed in a distal end of the needle.

The marker carrier is then unsheathed by retracting the outer sheath with respect to the marker carrier. An ejecting means is provided for ejecting the at least one marker from the marker carrier when the outer sheath is retracted relative to the marker carrier.

In this way, the position of the lesion is denoted by the at least one marker.

The at least one marker is preferably provided in the form of a hollow or solid member of predetermined configuration. In a hollow embodiment, the interior is filled with a radiopaque material, and the walls of the hollow marker are formed of a bioabsorbable material. A solid marker may be formed by pre-mixing a radiopaque material and a bioabsorbable material. In both hollow and solid embodiments, a dye or a radioactive material may replace or be used in conjunction with the radiopaque material.

In a preferred embodiment, the at least one marker is flexible, resilient and under compression when the marker carrier is ensheathed within the outer sheath. Accordingly, the means for ejecting the at least one marker includes the inherent bias of the at least one marker when the outer sheath is retracted relative to the marker carrier.

The marker carrier preferably has a recess of predetermined depth formed in an outer surface thereof for holding the at least one marker. The outer sheath has an internal diameter slightly greater than an external diameter of the marker carrier, and the at least one marker has a predetermined thickness that exceeds the predetermined depth of the recess so that the at least one marker is under compression when the marker carrier is ensleeved within the outer sheath. In this way, the at least one marker is ejected from the recess under its inherent bias when the outer sheath is withdrawn relative to the marker carrier.

In those embodiments where the at least one marker does not eject itself from the marker carrier upon unsheathing thereof, numerous other alternative ejection means may be employed. In one embodiment of an alternative ejection means, a push rod is slideably disposed within the marker carrier. The push rod has an exterior diameter slightly less than an interior diameter of the marker carrier. The at least one marker has a radially innermost side that is positioned within the interior bore of the marker carrier so that slideably introducing the push rod into the interior bore of the marker carrier displaces the at least one marker out of its marker retaining means so that the at least one marker is deployed into the soft tissue and remains in the soft tissue when the marker carrier is withdrawn from the soft tissue.

It is an important object of the present invention to provide a marker that is less likely to migrate any substantial distance within the body vis a vis conventional markers.

Another major object is to provide a marker that never requires surgical removal.

An object closely related to the foregoing object is to provide a marker that is bioabsorbable and which therefore disappears completely from the body, leaving no trace.

Another significant object is to provide an implement for deploying markers that can be used in conjunction with industry standard biopsy devices.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a longitudinal sectional view of the novel tool for marking lesions; and FIG. 2 is a perspective view depicting the novel tool in use with a biopsy tool of the prior art.

DETAILED DESCRIPTION OF THE PREFERRED EMBODIMENT

Referring now to FIG. 1, it will there be seen that an illustrative embodiment of the present invention is denoted as a whole by the reference number 10.

The novel tool 10 of this invention includes an elongate, flexible outer sheath 12, an elongate, flexible marker carrier 14, a plurality of markers 16, and a marker pusher 18.

As best understood in connection with FIG. 2, novel tool 10 has utility in conjunction with any prior art biopsy device 20. Tool 10 is inserted into the proximal end 22 of a biopsy needle 24 until distal end 13 of flexible outer sheath 12 extends through port 26 formed near the distal end of said biopsy needle 24.

The initial insertion procedure just described is the procedure used in the prior art for delivering metallic markers to the lesion site. In one popular tool, a pair of jaws holds a metallic marker until it has been delivered through port 26 to the site, and a mechanism operated by the physician opens the jaws to deposit the metallic marker.

Novel tool 10, however, includes no metallic marker or jaws. Markers 16 are nonmetallic. They may be hollow or solid and may be of any predetermined configuration, including spherical, cubical, pyramidal, pentagonal, and so on, including irregular forms. They may migrate even less when in a non-spherical form.

When in hollow form, they are filled with a radiopaque liquid and their outer walls are formed of a bioabsorbable material. When in solid form, they may be made by pre-mixing together a radiopaque material and a bioabsorbable material. In both embodiments, the radiopaque material, such as iodine, is also bioabsorbable.

One or more of the hollow markers may also be filled with an intense, bioabsorbable dye of blue or other easy-to-see color so that, upon being punctured, the stain would mark the tissue to be surgically removed. If such a dye were used, some of the markers would be filled with dye and some would be filled with a radiopaque material.

Alternatively, one or more of the hollow markers could be filled with radioactive powder, pellets, or liquid so that, once positioned within a lesion known to be malignant, the lesion could be treated by the radiation so provided, in a manner similar to procedures now used to treat malignancies in prostate glands In the embodiments where the markers are hollow, the outer wall thereof is made of a biodegradable and bioabsorbable material such as polylactite acid, polyglycolic acid, and equivalent materials. Other suitable materials include bioabsorbable copolymers of poly-dioxanone, copolymeric p-dioxanone/glycolide fibers, and other homopolymers and copolyesters derived from p-dioxanone. Moreover, additional suitable absorbable, synthetic polymers include poly-trimethylene carbonate, glycolide-trimethylene carbonate copolymer, and hydrogels. Those skilled in the art of materials will be aware of other equivalent materials not specifically listed herein, and all such additional bioabsorbable materials are within the scope of this invention.

The same materials identified in the preceding paragraph, including said equivalent materials, are also usable in the embodiment where the markers are solid. Such bioabsorbable materials are pre-mixed with a suitable radiopaque material to form a solid marker which in some formulations may have a gel-like consistency. Such bioabsorbable materials may also be pre-mixed with a dye or a radioactive material, as in the hollow marker embodiments.

In other words, in both the hollow and solid embodiments, the markers are preferably formed of a bioabsorbable material and one or more materials taken from a group of materials including radiopaque materials, dyes, and radioactive materials.

The jaws and other mechanical means for carrying the metallic markers of the prior art cannot be used to carry the novel markers because such jaws and other implements could puncture them before they could be properly deployed.

The preferred structure for carrying novel markers 16 includes elongate, flexible outer sheath 12, marker carrier 14, and push rod 18 as aforesaid. Carrier 14 and push rod 18 are also elongate and flexible so that they may flex in the manner depicted in FIG. 2 when in use.

Marker carrier 14 is generally tubular in configuration and has an internal bore of predetermined diameter. It includes at least one recessed structure or marker retaining means 15 for carrying a marker 16. In the preferred embodiment, there are a plurality of recessed structures 15 so that a plurality of markers 16 may be deposited in the vicinity of a lesion. This enhances the marking of the lesion and therefore facilitates surgical removal thereof if the lesion is determined to be malignant.

Recessed structure 15 is a frame-like structure having radially-inwardly extending legs 15a and longitudinally extending sections 15b that interconnect said legs 15a at their radially innermost ends. Each frame-like structure 15 includes four legs 15a and two longitudinally-extending sections 15b, all of said parts not being visible in the side view provided by FIG. 1. Each structure 15 is open at its bottom or radially innermost part. Moreover, in this preferred embodiment, each set of longitudinally-spaced apart legs 15a, 15a are angled so that they are closer together at the exterior surface of the marker carrier than at their respective radially innermost ends. This configuration serves to retain the markers within their respective marker retainer means when they are initially loaded into said marker carrier.

The first step of the novel procedure is to load at least one marker 16 into its associated retainer means. Marker carrier 14 is then slideably inserted into outer sheath 12. Preferably, the radial extent or thickness of each marker 16 exceeds the depth of its retainer means 15 so that the marker is under compression when marker carrier 14 is ensleeved within outer sheath 12. Tool 10 is then inserted through port 26 of biopsy needle 24 as indicated in FIG. 2. Outer sheath 12 is then retracted relative to marker carrier 14. Depending upon the size and resilience of markers 16, and depending upon the construction of the frame-like structure 15 that retains each marker, the markers may pop out of their respective retainer means 15 upon retraction of outer sheath 12, under their own inherent bias. If that happens, the procedure is finished and tool 10 is withdrawn.

If markers 16 do not pop out of their respective retainer means under their own inherent bias, then marker push rod 18 is advanced through the bore of marker callier 14 toward the distal end thereof as indicated by directional arrow 19. Since frames 15 are open-bottomed, such advancement will dislodge the markers from their respective frames and deploy them into the tissue in the vicinity of the lesion. Marker carrier 14 and push rod 18 are then withdrawn and the marking procedure is finished.

There are numerous mechanical means for causing markers 16 to exit frames 15 upon retraction of outer sheath 12. As already mentioned, the markers could be squeezed into their respective frames 15 by the interior cylindrical surface of outer sheath 12 so that when said outer sheath 12 is withdrawn, said markers exit their frames under their own inherent bias. Alternatively, frames 15 could be provided with a bottom wall, instead of having no bottom wall as depicted, and a small coil or leaf spring or other bias means could be positioned atop said bottom wall so that it underlies its associated marker. Withdrawal of outer sheath 12 would then allow said bias means to unload, thereby driving its associated marker out of its frame. The use of push rod 18 is preferred because it is less mechanically complex than a spring-based ejection system.

In those eighty per cent of cases where the lesion is benign and no surgery to remove it is required, markers 16 will biodegrade. The iodine therewithin, a nutrient, will be absorbed into the bloodstream. The polylactite acid, or other suitable material, although not a nutrient, will be similarly absorbed. In this way, no remnant of the marker remains in the breast tissue, and no potentially dangerous migration can occur as is the case with metallic markers.

Moreover, the novel tool disclosed herein is capable of delivering multiple markers to a lesion site, whereas the tools heretofore known are only capable of delivering a single marker at a time.

It will be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A method for delivering to a biopsy site a plurality of markers that indicate the location of a lesion in soft tissue, comprising the steps of:

providing an elongate, flexible outer sheath of generally tubular configuration;

providing an elongate, flexible marker carrier that is slideably received within said outer sheath;

forming a plurality of marker retaining means in said marker carrier and positioning a marker in each marker retaining means of said plurality of marker retaining means;

providing each marker in the form of a solid member of predetermined configuration, and forming each marker by pre-mixing together a bioabsorbable material and another material from the group including a radiopaque material, a dye, and a radioactive material;

introducing said outer sheath and marker carrier ensleeved therewithin into an open proximal end of a needle of a biopsy device and advancing said outer sheath until a distal free end thereof extends through a port formed in a distal end of said needle;

unsheathing said marker carrier by retracting said outer sheath with respect to said marker carrier;

providing a means for ejecting each marker from said marker carrier when said outer sheath is retracted relative to said marker carrier; and ejecting each marker from said marker carrier;

whereby the position of said lesion is denoted by said markers.

2. The method of claim 1, wherein each marker is flexible and resilient and under compression when said marker carrier is ensheathed within said outer sheath, whereby said means for ejecting said markers includes the inherent bias of the markers when said outer sheath is retracted relative to said marker carrier.

3. An apparatus for depositing a plurality of markers in the vicinity of a lesion, comprising:

an elongate, flexible outer sheath of generally tubular configuration;

an elongate, flexible marker carrier slideably disposed within said outer sheath;

a plurality of markers formed of a flexible and resilient material;

each marker of said plurality of markers being formed of a bioabsorbable material, and including a material preselected from a group including a radiopaque liquid, a radioactive material, and a dye;

said marker carrier having a plurality of recesses of uniform predetermined depth formed in an outer surface thereof for respectively holding said plurality of markers;

said outer sheath having an internal diameter slightly greater than an external diameter of said marker carrier;

each marker of said plurality of markers having a predetermined thickness that exceeds the uniform predetermined depth of said recesses so that each marker is under compression when said marker carrier is ensleeved within said outer sheath;

whereby each marker is ejected from its recess under its inherent bias when said outer sheath is withdrawn relative to said marker carrier.

4. The apparatus of claim 3, wherein each marker is a solid member of predetermined configuration formed by pre-mixing together at least two materials including a bioabsorbable material and another material from the group including a radiopaque material, a dye, and a radioactive material.

5. The apparatus of claim 3, wherein each of said markers has a hollow construction including an outer wall formed of a biodegradable material and wherein each of said markers is filled with a detectable material.

6. An apparatus for depositing a plurality of markers in the vicinity of a lesion, comprising:

an elongate, flexible outer sheath of generally tubular configuration;

an elongate, flexible marker carrier slideably disposed within said outer sheath, said marker carrier having a generally tubular configuration and defining an interior bore of uniform diameter;

a plurality of marker retaining means formed in said marker carrier for holding a plurality of markers;

each marker of said plurality of markers being formed of a bioabsorbable material, and including a material selected from a group including a radiopaque liquid, a radioactive material, and a dye;

a push rod slideably disposed within said marker carrier, said push rod having an exterior diameter slightly less than an interior diameter of said marker carrier;

each marker having a radially innermost side that is positioned within said interior bore of said marker carrier;

whereby slideably introducing said push rod into said interior bore of said marker carrier respectively displaces each marker out of said marker retaining means so that each marker is deployed into said soft tissue and remains in said soft tissue when said marker carrier is withdrawn from said soft tissue.

7. The apparatus of claim 6, wherein each of said markers is solid and formed by pre-mixing together at least two materials including a bioabsorbable material and another material from the group including a radiopaque material, a dye, and a radioactive material.

8. The apparatus of claim 6, wherein each of said markers has a hollow construction including an outer wall formed of a biodegradable material and wherein each of said markers is filled with a detectable material.

* * * * *